United States Patent [19]

Fletcher et al.

[11] 4,118,315

[45] Oct. 3, 1978

[54] WATER SYSTEM VIRUS DETECTION

[76] Inventors: James C. Fletcher, Administrator of the National Aeronautics and Space Administration with respect to an invention of; Alan S. Fraser, Whittier; Arthur F. Wells, Upland; Harold J. Tenoso, Burbank, all of Calif.

[21] Appl. No.: 792,068

[22] Filed: Apr. 28, 1977

[51] Int. Cl.$^2$ .................. B01D 13/00; B01D 31/00
[52] U.S. Cl. .................. 210/23 F; 210/96 M; 210/433 M
[58] Field of Search ............ 195/103.5 V; 210/96 R, 210/23 F, 433 M

[56] References Cited

U.S. PATENT DOCUMENTS

| | | | |
|---|---|---|---|
| 3,127,329 | 3/1964 | Andersen | 195/103.5 V |
| 3,250,596 | 5/1966 | Grafe | 195/103.5 V |
| 4,018,652 | 4/1977 | Lanham et al. | 195/103.5 V |

OTHER PUBLICATIONS

"Biological Analysis of Water and Waste Water", Millipure Manual, AM 302, pp. 63–72.

*Primary Examiner*—Frank A. Spear, Jr.
*Attorney, Agent, or Firm*—Marvin J. Marnock; John R. Manning; Marvin F. Matthews

[57] ABSTRACT

The performance of a waste-water reclamation system is monitored by introducing a non-pathogenic marker virus, bacteriophage $F_2$, into the waste-water prior to treatment and, thereafter, testing the reclaimed water for the presence of the marker virus. A test sample is first concentrated by absorbing any marker virus onto a cellulose acetate filter in the presence of a trivalent cation at low pH and then flushing the filter with a limited quantity of a glycine buffer solution to desorb any marker virus present on the filter. Photo-optical detection of indirect passive immune agglutination by polystyrene beads indicates the performance of the water reclamation system in removing the marker virus. A closed system provides for concentrating any marker virus, initiating and monitoring the passive immune agglutination reaction, and then flushing the system to prepare for another sample. Peristaltic pumps are provided for volumetric control and for positive fluid displacement. Solenoid valves direct the output from the pumps in preselected routes to accomplish the process for concentrating and detecting the marker virus.

16 Claims, 3 Drawing Figures

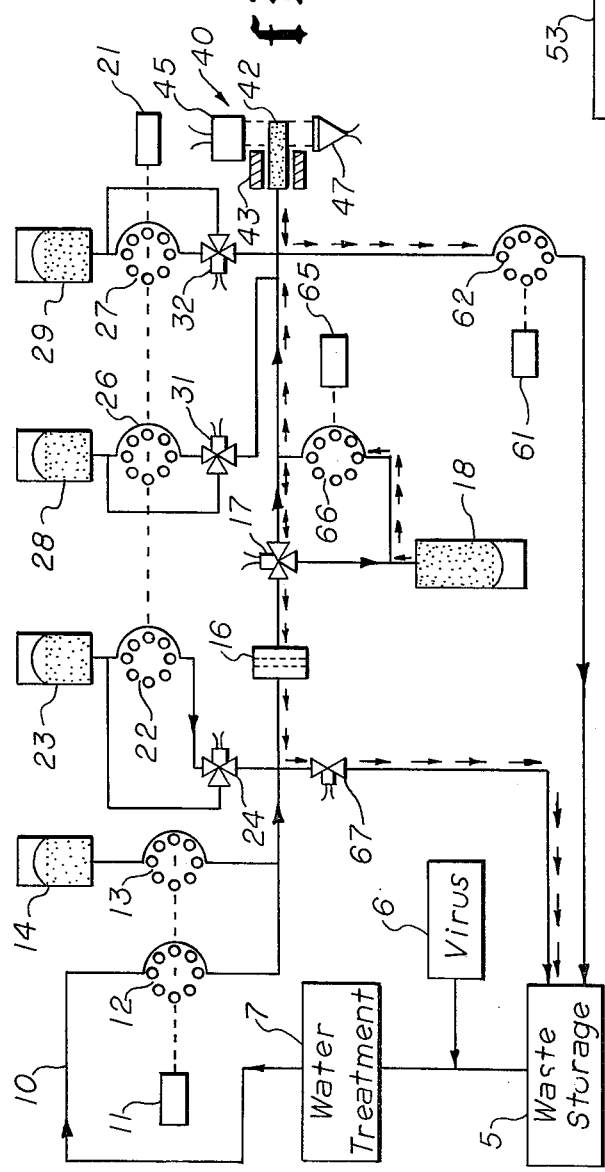
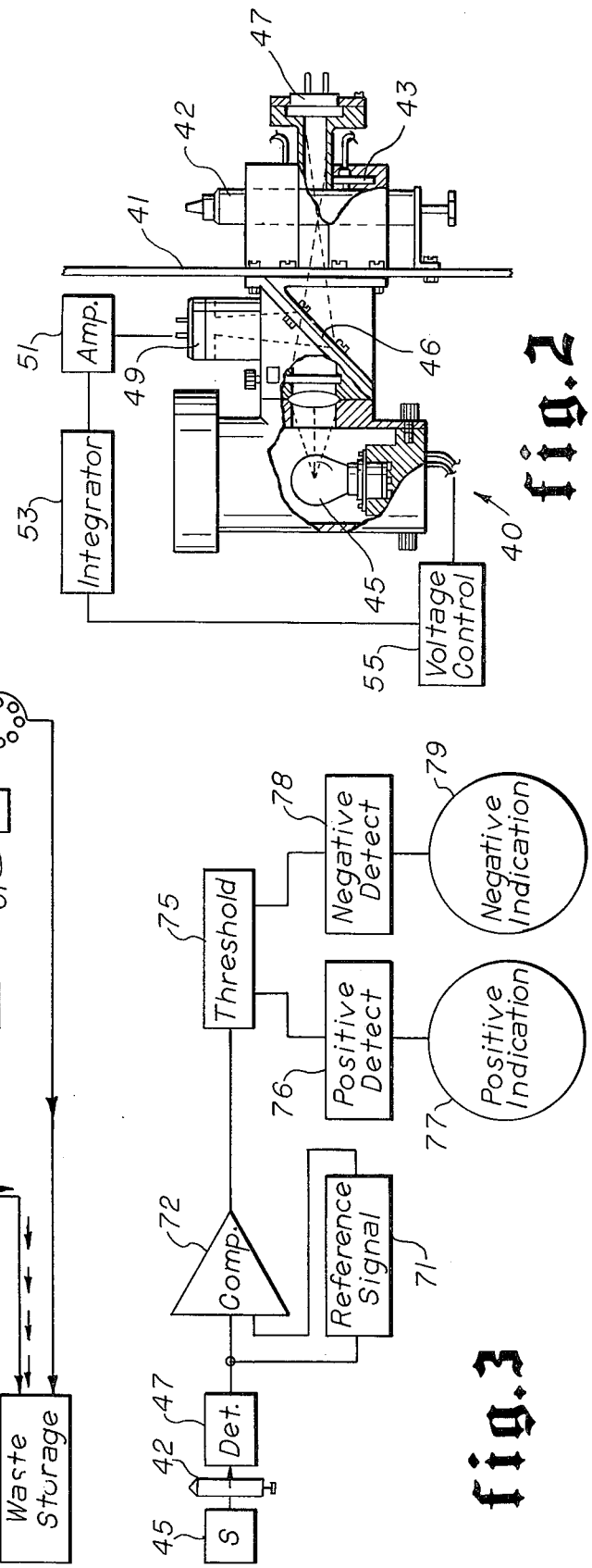

4,118,315

WATER SYSTEM VIRUS DETECTION

ORIGIN OF THE INVENTION

The invention described herein was made in the performance of work under a NASA contract and is subject to the provisions of § 305 of the National Aeronautics and Space Act of 1958, Public Law 85-568 (72 Stat.435; 45 USC 2457).

BACKGROUND OF THE INVENTION

This invention relates to performance monitoring of a waste-water reclamation system, and more particularly to monitoring the performance of a waste-water reclamation system in removing a known marker virus by injecting a known quantity of the marker virus upstream and detecting the presence of the virus downstream from the reclamation system.

In a closed environment system, such as exists in a spacecraft, it is necessary to recycle waste products to the maximum extent in order to fully utilize all the expendable products carried on board. Water is a particular commodity which must be recycled because of the space and weight required to carry large amounts. Waste-water for recycling is available from such sources as wash water, urine, and environmental humidity.

There are many systems well known in the prior art which can treat the above sources of waste water to remove the waste products and provide a recycled source of water. It is necessary, however, to monitor performance of any reclamation system in order to insure that the reclaimed water is indeed free of contamination and, in particular, free from pathogenic viruses which could contaminate the crew members.

Since the presence of a virus in the purification system output is potentially the most dangerous result of a system malfunction, it is desirable to monitor the output for the presence of a virus. The particular virus selected for monitoring must be such that it will survive any waste-water environment and be generally a worse-case virus with respect to the ability of the purification system to remove the virus. The system output is then monitored for the presence of the selected virus. It is desirable that the monitoring system be able to detect a very low level of failure in the purification system while retaining a high degree of simplicity and reliability.

It is an object of the present invention to detect the presence of a marker virus in reclaimed water.

It is yet another feature of the present invention to monitor the performance of a waste water reclamation system whereby early detection of any system malfunction is obtained.

It is yet another feature of the present invention to process the sample from the output of the purification system in a closed detection system to monitor system performance.

It is a feature of the present invention to detect the presence of a known virus in the output of a waste water reclamation system to ascertain the possible presence of pathogenic viruses in the output.

Still another feature of the present invention is a monitoring system capable of being incorporated in a spacecraft and retaining its efficacy over extended periods of time.

SUMMARY OF THE INVENTION

A monitoring method and system is presented to test the capability of a water reclamation system to reject the passage of viruses with the reclaimed water. In a preferred embodiment of the method which is the subject of the present invention, a non-pathogenic marker virus is fed into the process stream upstream of the water recovery unit and the reclaimed water is tested to determine the absence of the marker virus. The marker virus selected, bacteriophage $F_2$, provides for a worst-case condition so that the absence of the marker virus in the reclaimed water provides assurance of the absence of any naturally occurring human pathogenic viruses. A failure in the water reclamation system will result in the passage of some quantity of marker virus through the system. It is contemplated by the present invention to detect the passage of only 1/10,000 of the marker virus present in the waste water.

Detection of the marker virus in the downstream water consists of two major steps: (1) concentrating any marker virus which may be present and (2) obtaining an indication of the presence of the virus. Concentrating the marker virus requires that the virus be first removed from the reclaimed water sample. This is accomplished by adsorbing the marker virus onto the surface of a cellulose acetate filter in the presence of a low pH solution with a trivalent cation. A limited quantity of a high pH buffer solution is then passed through the cellulose filter to desorb any marker virus on the filter surface and thereby obtain an increased concentration of virus in the sample passed to the detection step.

An indication of the presence of marker virus in the buffer solution is now obtained utilizing the passive immunological reaction which occurs between a virus and the antibody for that virus. The presence of the reaction may be detected by a method known as passive immune agglutination wherein small latex or polystyrene beads are coated with the virus or antibody and dispersed in a suitable medium. This dispersion is then mixed with a solution to be tested. If the test solution contains material reactive with the material on the beads, the reaction will cause the beads to agglutinate. The occurrence of agglutination will change the light transmittance of the bead dispersion which can be detected by means of conventional optical detection equipment.

BRIEF DESCRIPTION OF THE DRAWINGS

In order that the manner in which the above recited features of the invention are obtained can be understood in detail, a more particular description of the invention may be had by reference to the specific embodiment thereof which are illustrated in the appended drawings, which drawings form a part of this specification. It is to be noted, however, that the appended drawings illustrate only typical embodiments of the invention and, therefore, are not to be considered limiting of its scope for the invention may admit to further equally effective embodiments.

In the Drawings

FIG. 1 is a simplified schematic diagram of the reclaimed water virus detection system according to one embodiment of the present invention.

FIG. 2 is an elevation view, partly in cross-section, of an optical detector assembly utilized in the detection system.

FIG. 3 is a simplified schematic of a system for monitoring the optical detector output.

DETAILED DESCRIPTION OF THE PREFERRED EMBODIMENT

The reclaimed water virus detection system which is the subject of the present invention embodies the introduction of a sufficient concentration of a marker virus upstream of a purification system and the subsequent downstream detection of any remaining marker virus such that a failure in the purification system can be promptly detected. To provide adequate protection, it is desirable that the system be able to detect the passage of only 1/10,000 of the marker virus introduced upstream of the purification system.

The quantity of marker virus to be added to each batch of waste water to be reclaimed must be such that the desired 1/10,000 reduction factor for detection can be achieved. The system which is the subject of the present invention, and hereinbelow described, can detect a concentration of marker virus of $1 \times 10^9$ PFU/ml (plaque forming units per milliliter) in the detection sample. The detection sample is derived from a test sample of the reclamation system output wherein the concentration of marker virus is increased by 100 times. Accordingly, the presence of only $1 \times 10^7$ PFU/ml of marker virus in the reclaimed water can be detected. Since this is to represent a reduction of $1 \times 10^{-4}$ from an input concentration, the input concentration of marker virus to the reclamation system must be $1 \times 10^{11}$ PFU/ml. If the volume of waste water is known, then the quantity of marker virus necessary to add to the waste water to yield the input concentration can be easily determined.

The marker virus selected for use in the virus detection system is known as bacteriophage $F_2$. This virus is non-pathogenic to humans so no danger of contamination exists from this viral source. Further, the selected virus is about the same size as, or smaller then, pathogenic viruses commonly encountered in humans and possesses a relatively high resistance to possible environmental conditions imposed by the water reclamation process, thereby lending itself to an ideal "worst-case" test.

Referring now to FIG. 1, there may be seen a simplified schematic of the reclaimed water virus detection system which is the subject of the present invention. Reclaimed water 10 is first presented to the detection system after being passed from the waste storage tank 5 through the water treatment system 7. The object of the method and apparatus, hereinbelow discussed, is to detect the presence of any marker virus remaining in the water after the purification process. In fact, the detection system determines the presence of the marker virus in the system by providing a positive indication of the absence of the virus.

Waste water from various sources, such as wash water, body waste and atmospheric maintenance systems, is accumulated in storage tank 5 until a sufficient quantity is available to process through the treatment system. Just prior to treatment, marker virus injection system 6 injects a sufficient quantity of marker virus to provide a marker virus concentration of $1 \times 10^{11}$ PFU/ml in the input to water treatment system 7.

In the first step of the monitoring process, the reclaimed water sample must be treated to concentrate any marker virus for presentation to the remainder of the system. The concentration step is accomplished by using a cellulose acetate filter 16 to adsorb the marker virus on the filter surface as the sample is passed through the filter. A suitable filter may be obtained from Millipore Corporation with a porosity of 0.45 microns and a diameter of 25 mm. To aid the adsorption of the marker virus onto the filter, a trivalent cation in a low pH solution is mixed with the waste water sample for presentation through the filter. A suitable trivalent cation has been found to be aluminum chloride ($AlCl_3$). A preferred waste water solution contains 5 mM aluminum chloride and acid to achieve a pH of 2.5–3.0 in the sample. Satisfactory adsorption of the marker virus onto filter 16 is achieved with a solution of 0.5 mM $AlCl_3$ but an increased concentration of 5.0 mM $AlCl_3$ enhances marker virus adsorption under certain waste water conditions.

Referring again to FIG. 1, sample pump 11 is activated to turn peristaltic rotor 12 to pump in the desired volume of reclaimed water sample with any marker virus and simultaneously turn peristaltic rotor 13 to introduce the low pH aluminum chloride from tank 14. The solution comprising the reclaimed water and trivalent cation flows through cellulose acetate filter 16 and three-way valve 17 which is actuated to direct the solution into catch tank 18. As the solution flows through filter 16, any marker virus are adsorbed onto the surface of the filter.

In the final step of the concentration process, a small quantity of a suitable buffer solution is next flowed through the cellulose acetate filter 16 to desorb the marker virus from the filter. In this step, valve 17 is activated to direct the fluid flow to the syringe portion 42 of optical detector assembly 40. Reagent pump 21 is actuated to drive peristaltic rotor 22, and valve 24 is opened for allowing the buffer solution from buffer supply tank 23 to flow through filter 16. A suitable buffer solution is 0.05 M glycine at a pH of 11.5 with a quantity of about 3 ml. pumped through filter 16. It has been found that the recovery of marker virus is enhanced if about 1 ml. is pumped through the filter and thereafter the remaining 2 ml. pumped through after a short delay period. Any marker virus collected on the cellulose acetate filter 16 are thereby removed in a concentrated form with the buffer solution and pumped into syringe 42.

Any marker virus concentrated in the test sample must now be detected. The method chosen for detection of the virus is the passive immune agglutination (PIA) technique. The basic theory behind the PIA method is that a link is developed between a virus and the antibody for that virus. If the virus or the virus antibody is first placed on small plastic beads in a suspension and the beads are then subjected to a solution containing the antigen of the bead coating, cross links develop between the material on the beads and the material in solution and cause the beads to agglutinate. This agglutination changes the light transmission characteristics of the resulting mixture and the agglutination can thus be detected either visually or by photo-optical instrumentation. In the direct PIA method, the beads are coated with the antibody and then exposed to the virus. If the mixture is then incubated, and the virus is present, the antibodies on the beads will cross link with the virus in the sample and bead agglutination will occur. Although the direct PIA technique provides a positive indication of the presence of the marker virus over a certain range of concentrations, a secondary effect occurs which makes this method less desirable. If a large amount of marker virus is present, all of the antibodies on a given bead become complexed with the virus so that cross linking and agglutination do not occur and a false negative indication is obtained.

For the above reason, an indirect PIA method was selected as the preferred embodiment. In this method the beads are generally latex or polystrene beads of about 1.1 micron diameter and are first coated with the marker virus. The concentrated test sample is mixed with a solution containing a predetermined concentration of the virus antibody selected to match the concentration of virus to be detected and the mixture is incubated for a predetermined time. The virus coated beads are then introduced to the incubated mixture. If a virus is present in the sample, the antibodies are neutralized and no antibodies are available to cross link with the virus on the beads. If there is no virus in the test sample, antibodies remain available to react with the marker virus on the beads and cause agglutination of the beads. Thus, the absence of a sufficient quantity of marker virus generates a positive indication, i.e., bead clumping or agglutination.

Referring again to FIG. 1, the PIA test is initiated simultaneously with desorption of the marker virus from filter 16. When reagent pump 21 is actuated, peristaltic rotors 26 and 27 pump the antibody solution from tank 28 and the virus coated bead solution from tank 29, respectively. Three-way valve 31 is first energized to allow a predetermined amount of antibody solution into syringe 42 to react with any marker virus concentrated in the test sample. Valve 32 is energized thereafter to allow a predetermined amount of bead solution into the reacted solution. These solutions are all collected in syringe 42 along with the buffer solution containing any marker virus desorbed from filter 16.

The sensitivity of the system is determined by the tendency of the beads to agglutinate in the presence of free antibodies. This tendency is functionally related to the concentration of the antibodies in the solution and also to the dilution of the beads in suspension. It has been found that the ability to detect bead agglutination is optimum at a bead dilution of about 1:1,000 from a stock concentration of about 3–5 mg/ml. However, it has also been determined that agglutination does not readily occur in this system with bead dilutions over 1:900. Therefore, a bead dilution of 1:900 was selected for the preferred embodiment. The antibody concentration is matched to the upper level of virus concentration which the system must be able to detect. The higher the antibody concentration, the higher the detection threshold for the system. It has been determined that an antibody dilution of 1:3,200 from a stock concentration of antibody and combined with the optimum bead dilution provides the desired system detection capability.

The virus-coated beads and the antibodies are both carried in solutions of 0.1 M glycine, 1% NaCl pH 8.2. If it is desired to maintain the marker virus and antibodies for extended time periods, the resulting solutions may be refrigerated to a temperature of about 4° C. for storage.

Referring yet again to FIG. 1, the solution containing free antibodies, if any, and coated beads is contained in syringe 42 within optical detector assembly 40 where it is maintained at a temperature of 45° C. by heater 43 for 5 hours. Light source 45 directs light through the incubated sample to a detector 47 for measuring the change in light transmittance through the sample. The base light transmittance is taken as the light transmittance at the beginning of the incubation time and the change in light transmittance is measured as a function of time. The effect of agglutination is to increase the light transmittance and, hence, the effect of an operable purification system is a positive indication of agglutination.

Referring now to FIG. 2, there may be seen an elevation view, in partial cross-section, of an optical detector assembly used to detect agglutination of the beads. Optical detector assembly 40 generally includes a housing assembly 41 in which all the components are mounted and is secured to a suitable protective package. The sample for the PIA test is contained in syringe 42 mounted in housing 41. A light source 45 is provided and the light output is directed to a beam splitter 46. One output from the beam splitter 46 is directed to photo-detector 49 and used as a feedback signal to maintain a constant light intensity from light source 45 through conventional electronic circuitry wherein the output from detector 49 is increased by amplifier 51 and passed to integrator 53 for comparison with a reference in voltage control circuit 55 to regulate the voltage supplied to light source 45. Another portion of the light beam from beam splitter 46 is directed through the solution in syringe 42. The light transmitted through syringe 42 is detected by photo-detector 47 and processed through conventional electronic circuitry, discussed hereinbelow to obtain an output indication of the light transmittance. The reference light transmittance is that transmittance at the beginning of the incubation period. Heater 43 is activated to maintain the test sample at about 45° C. during the 5 hour incubation period. The light transmittance is monitored throughout the incubation period to ascertain the occurrence of agglutination of the beads. As hereinabove explained, the occurrence of agglutination indicates the absence of marker virus in the reclaimed water sample.

Referring now to FIG. 3, there may be seen a simplified schematic of a circuit to detect changes in the output of photo-detector 47. At the beginning of the incubation period, a reference signal is generated by reference circuit 71. When a predetermined change in the light transmittance through syringe 42 has occurred, the output from comparator 72 will be sufficient to trigger threshold circuit 75. The output from threshold circuit 75 drives circuits 76 and 78 which provide a positive and negative signal respectively. The occurrence of a positive signal to circuit 76 results in a positive indication 77 of the presence of marker virus. Similarly, the occurrence of a negative signal to circuit 78 results in a negative indication 79, i.e., the absence of marker virus.

Referring again to FIG. 1, the remaining steps in the process include removing the incubated test sample and preparing the system to receive another sample. Accordingly, waste pump 61 is activated to turn peristaltic rotor 62 to pump the incubated sample material back to the waste tank 5 in the reclamaion system. Subsequently, rinse pump 65 is activated to turn peristaltic rotor 66 to flush the original test sample material through the system. Valve 67 is opened and the material contained in holding tank 18 is pumped through valve 17 and filter 16 to regenerate the filter and out through valve 67 to return to the purification system for reprocessing. The system is now flushed and ready to receive another test sample.

In the preferred operation of the detection system, after a selected concentration of marker virus is injected upstream of the water purification system 7, a 400 ml. processed water sample is pumped through cellulose acetate filter (25 mm.) 16 at 20 ml. per minute and collected in tank 18. Before passing through filter 16, an aluminum chloride and acid concentrate is added at 0.5 ml. per minute which lowers the pH to 2.5–3.0 and adds 5 mM $AlCl_3$. Following the initial 400 ml. of treated sample, an additional 10 ml. of untreated sample is pumped through the filter to remove residual aluminum chloride, which has been shown to interfere with the PIA detection system. To remove any virus adsorbed on filter 16, 3.0 ml. of 0.05 M glycine buffer, pH 11.5, is pumped through filter 16 at 30 ml. per minute. The first milliliter is pumped through and collected in syringe 42, with the next 2 milliliters collected after a 1 minute delay. This delay was incorporated since it appears to increase the overall efficiency of marker virus desorption. To the 3.0 ml. marker virus concentrate in syringe 42, 1.0 ml. of a predetermined dilution of marker virus antibody is added and the mixture incubated for ½ hour at 45° C. Following this reaction period, 1.0 ml. of a predetermined dilution of 1.1 micron latex or polystyrene beads coated with marker virus is added and a spectro-photometric reading is made to determine the base light transmission of the suspension. The mixture is then incubated for 5 hours at 45° C., during which the light transmission through the solution is compared with the original reading. An increase in light transmission is indicative of bead agglutination and, therefore, the absence of marker virus in the concentrate.

Numerous variations and modifications may obviously be made in the structure herein described without departing from the present invention. Accordingly, it should be clearly understood that the forms of the invention herein described and shown in the figures of the accompanying drawings are illustrative only and are not intended to limit the scope of the invention.

What is claimed is:

1. A process for monitoring the performance of a water recovery purification system in removing pathogenic viruses, said process comprising the steps of:
- introducing a non-pathogenic bacteriophage marker virus at a predetermined concentration upstream of said water recovery system;
- collecting a sample of effluent from said water recovery system;
- concentrating any marker virus present in said effluent sample by mixing said sample with a solution containing a trivalent cation formed from a solution containing $AlCl_3$ to obtain a resulting mixture with a pH of 2.5–3.5,
- passing said resulting mixture through a cellulose acetate filter to adsorb any of said marker virus onto said filter, and thereafter
- desorbing any of said marker virus from said filter by passing a selected quantity of a buffer solution through said filter to form a solution containing an increased concentration of said virus; and
- testing said concentrated sample for said marker virus to monitor said water recovery purification system.

2. The process as described in claim 1, including the step of forming said trivalent cation from a solution containing 0.5–5.0 mM $AlCl_3$.

3. The process as described in claim 1, wherein the step of testing said concentrated sample comprises the steps of:
- reacting an antibody of said marker virus with said marker virus to determine the presence of said marker virus in said concentrated sample, and
- detecting the reaction between said antibody and said virus to indicate a failure in said purification system.

4. The process as described in claim 3, wherein the step of reacting said antibody and said virus comprises the steps of:
- preparing a suspension containing inert beads coated with said antibody at a predetermined concentration, and
- exposing said bead suspension to said concentrated sample to obtain a passive immune agglutination of said beads if a preselected concentration of said marker virus is present in said concentrated sample.

5. The process as described in claim 3, wherein the step of reacting said antibody and said virus comprises the steps of:
- preparing a suspension containing inert beads coated with said marker virus at a predetermined concentration,
- reacting a solution of said concentrated sample and a solution containing a predetermined concentration of said antibody, thereafter mixing said bead suspension with said reacted sample to form a detection sample, and
- incubating said detection sample to obtain a passive immune agglutination of said beads if the concentration of said marker virus in said concentrated sample is below a preselected level.

6. The process as described in claim 5, wherein the step of detecting said reaction between said marker virus and said antibody comprises the steps of:
- measuring the light transmittance of said incubating detection sample at the beginning of said incubation,
- continuing to incubate said detection sample for a predetermined time to produce a passive immunization reaction, and
- measuring the light transmittance of said incubating detection sample to detect a change in said light transmittance resulting from a passive immune agglutination within said incubating detection sample.

7. The process as described in claim 1, wherein said marker virus is bactriophage $F_2$.

8. A process for monitoring the presence of a known virus in a water sample, comprising the steps of:
- mixing said sample with a solution containing a trivalent cation formed from a solution containing $AlCl_3$ to obtain a resulting mixture with a pH of 2.5–3.5,
- passing said resulting mixture through a cellulose acetate filter to adsorb any of said virus onto said filter,
- desorbing any of said known virus from said filter by passing a limited quantity of a buffer solution through said filter to form a concentrated solution containing said virus,
- reacting an antibody of said known virus in said concentrated sample, and
- photo-optically detecting the reaction between said antibody and said virus to indicate the presence of said known virus in said sample.

9. The process as described in claim 8, wherein the step of reacting said antibody and said virus comprises the steps of:
- preparing a suspension containing inert beads coated with said antibody at a predetermined concentration, and exposing said bead suspension to said concentrated sample to obtain a passive immune agglutination of said beads if a preselected concentration of said known virus is present in said concentrated sample.

10. The process as described in claim 8, wherein the step of reacting said antibody and said known virus comprises the steps of:
preparing a suspension of inert beads coated with said known virus at a predetermined concentration,
reacting a solution of said concentrated sample and a solution containing a predetermined concentration of said antibody,
mixing said bead suspension with said reacted sample to form a detection sample,
incubating said detection sample to obtain a passive immune agglutination of said beads if the concentration of said known virus in said concentrated sample is below a preselected level.

11. The process, as described in claim 10, wherein the step of photo-optically detecting the reaction between said antibody and said virus includes:
measuring the initial light transmittance of said incubating detection sample to obtain a reference transmittance,
continuing to incubate said detection sample for a predetermined time at a preselected temperature to produce passive immune agglutination of said beads, and
measuring the light transmittance of said incubating detection sample to detect an increase in said light transmittance which indicates the occurrence of passive immune agglutination and the absence of the known virus.

12. A system for monitoring the performance of a water recovery purification system for removing pathogenic viruses, comprising:
means for introducing a selected marker virus at a predetermined concentration upstream of said water recovery system,
a source of a low pH solution containing a trivalent cation,
a first pump cooperating with said source of a low pH solution for mixing a sample of effluent from said water recovery system with a predetermined quantity of said low pH solution,
a filter receiving the mixed output from said first pump for adsorbing any of said marker virus present in said effluent sample,
a source of a buffer solution,
a source of a solution containing an antibody for said marker virus,
a source of a suspension of beads coated with said marker virus,
valve means for receiving the outputs of said sources of said buffer solution, said virus antibody solution and said suspension of marker virus coated beads for selectively passing each of said buffer solution, virus antibody solution, and suspension of marker virus-coated beads,
sample collection means,
a second pump interconnected between said valve means, said filter and said sample collection means and cooperating with said valve means for first pumping a selected quantity of said buffer solution through said filter to desorb said marker virus from said filter to form a concentrated sample solution of marker virus deposited in said sample collection means, and then pumping predetermined quantities of said virus antibody solution and said suspension of marker virus-coated beads into said sample collection means for mixing with said concentrated virus sample,
heating means cooperating with said sample collection means for incubating said collected sample to produce passive immune agglutination of said beads, and
photo-optical detector means cooperating with said sample collection means for monitoring the light transmittance through said incubating collected sample and detecting the increase in said light transmittance caused by passive immune agglutination.

13. The system, as described in claim 12, wherein said first and second pump means each comprise peristaltic pumps.

14. The system as described in claim 12, wherein said filter comprises a cellulose acetate membrane.

15. The system as described in claim 12, wherein said sample collection means comprises a syringe for receiving and holding the collected sample solution.

16. The system as described in claim 12, wherein said photo-optical detector means further comprises:
a light source for directing a beam of light through said syringe and said incubating collected sample, and
detector means disposed opposite said syringe from said light source for receiving said light beam and deriving an indication of an increase in light transmittance due to a positive immune agglutination of said beads within said syringe.

* * * * *